(12) United States Patent
Kasai

(10) Patent No.: US 7,381,203 B2
(45) Date of Patent: Jun. 3, 2008

(54) DISPOSABLE DIAPER

(75) Inventor: Takao Kasai, Tochigi (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 10/530,705

(22) PCT Filed: Oct. 10, 2003

(86) PCT No.: PCT/JP03/13052

§ 371 (c)(1),
(2), (4) Date: Nov. 8, 2005

(87) PCT Pub. No.: WO2004/037144

PCT Pub. Date: May 6, 2004

(65) Prior Publication Data

US 2006/0122570 A1 Jun. 8, 2006

(30) Foreign Application Priority Data

Oct. 22, 2002 (JP) .......................... 2002-307537

(51) Int. Cl.
*A61F 13/15* (2006.01)
(52) U.S. Cl. ............ 604/385.24; 604/380; 604/385.26; 604/385.01; 604/385.25; 604/385.27
(58) Field of Classification Search .......... 604/385.24, 604/385.25, 385.26, 385.27, 385.28, 378, 604/379, 380, 385.01
See application file for complete search history.

(56) References Cited

U.S. PATENT DOCUMENTS 5,484,430 A * 1/1996 Osborn, III ............ 604/385.21
6,315,765 B1 * 11/2001 Datta et al. ............ 604/385.24
2002/0123732 A1 * 9/2002 Koyama et al. ....... 604/385.24
2003/0093045 A1 * 5/2003 Erdman ...................... 604/367

FOREIGN PATENT DOCUMENTS

| CN | 1313745 A | 9/2001 |
| JP | 63-102426 U | 7/1988 |
| JP | 3-121069 A | 5/1991 |
| JP | 11-216161 A | 8/1999 |
| JP | 11-513927 A | 11/1999 |

OTHER PUBLICATIONS

Microfilm of the specification and drawings annexed to the request of Japanese Utility Model Application No. 202240/1986 (Laid-open No. 102426/1988) (Wako Seishi Kabushiki Kaisha) Jul. 4, 1988.

* cited by examiner

*Primary Examiner*—Jacqueline F. Stephens
(74) *Attorney, Agent, or Firm*—Birch, Stewart, Kolasch, & Birch, LLP

(57) ABSTRACT

A disposable diaper (1) comprising a liquid permeable topsheet (2), a liquid impermeable backsheet (3), and liquid retentive absorbent members (41), (42), and (43) interposed between the two sheets, wherein the absorbent members (41) (42), and (43) are disposed in series in the direction of from the rear portion (B), through the crotch portion (A), to the front portion (C), an elastic member is disposed in its stretched state on both sides of the series of the absorbent members, and the absorbent members (41), (42), and (43) are arranged such that a gap is produced between any adjacent two of them when the diaper is stretched flat and that any adjacent two of the absorbent members come into close contact when the diaper is worn.

5 Claims, 4 Drawing Sheets

DISPOSABLE DIAPER

TECHNICAL FIELD

The present invention relates to a disposable diaper providing a snug fit with little bagging of its absorbent member while worn.

BACKGROUND ART

A disposable diaper generally has a one-piece, vertically long absorbent member disposed on an area from the rear portion, through the crotch portion, to the front portion. Elastic members are usually arranged on the leg portions to give an improved fit to wearer's legs for leakage protection.

In conventional disposable diapers, the leg portions contract with contraction of the elastic members whereas the absorbent member is not so contractible in its longitudinal direction because of its stiffness. As a result, the absorbent member sometimes becomes baggy (swelling outward) by the excess length while worn, which can cause inconveniences such as liquid's staying in the crotch portion, overhydration, and leakage. Because so-called fitted type (tape type) disposable diapers, in particular, are generally folded widthwise and compression packaged in a bag as folded for distribution and sale, the absorbent member gets oddly creased and more liable to bagging out when the diaper is worn.

JP-A-11-216161 proposes a disposable diaper in which an absorbent core is divided along imaginary lines extending in the diaper length direction and also along imaginary lines perpendicular to those imaginary lines. The absorbent core has a particle layer made mainly of a superabsorbent polymer and a fiber layer underlying the particle layer. If absorption by the particle layer results in gel blocking, further transfer of liquid to the fiber layer would be hindered. The division of the absorbent core aims to make the fiber layer capable of direct absorption from the side faces and to increase the total absorption area of the core. To achieve the aims, the gaps between divided sections of the core should be retained during use of the diaper. Therefore, the proposed disposable diaper is incapable of preventing bagging of the absorbent member and the resultant inconveniences while worn.

DISCLOSURE OF THE INVENTION

An object of the present invention is to provide a disposable diaper providing a snug fit with little bagging of its absorbent member while worn.

The above object is accomplished by a disposable diaper of the present invention. The disposable diaper of the present invention has a liquid permeable topsheet, a liquid impermeable backsheet, and a liquid retentive absorbent member interposed between the topsheet and the backsheet. The disposable diaper of the present invention has a plurality of the absorbent members disposed in series in the direction of from the rear portion, through the crotch portion, to the front portion of the diaper and also has an elastic member disposed in its stretched state on both sides of the series of the absorbent members. The absorbent members are arranged such that a gap is produced between any adjacent two of the absorbent members when the diaper is stretched flat and that the adjacent two of the absorbent members come into close contact with each other when the diaper is worn.

BRIEF DESCRIPTION OF THE INVENTION

Figure 1:
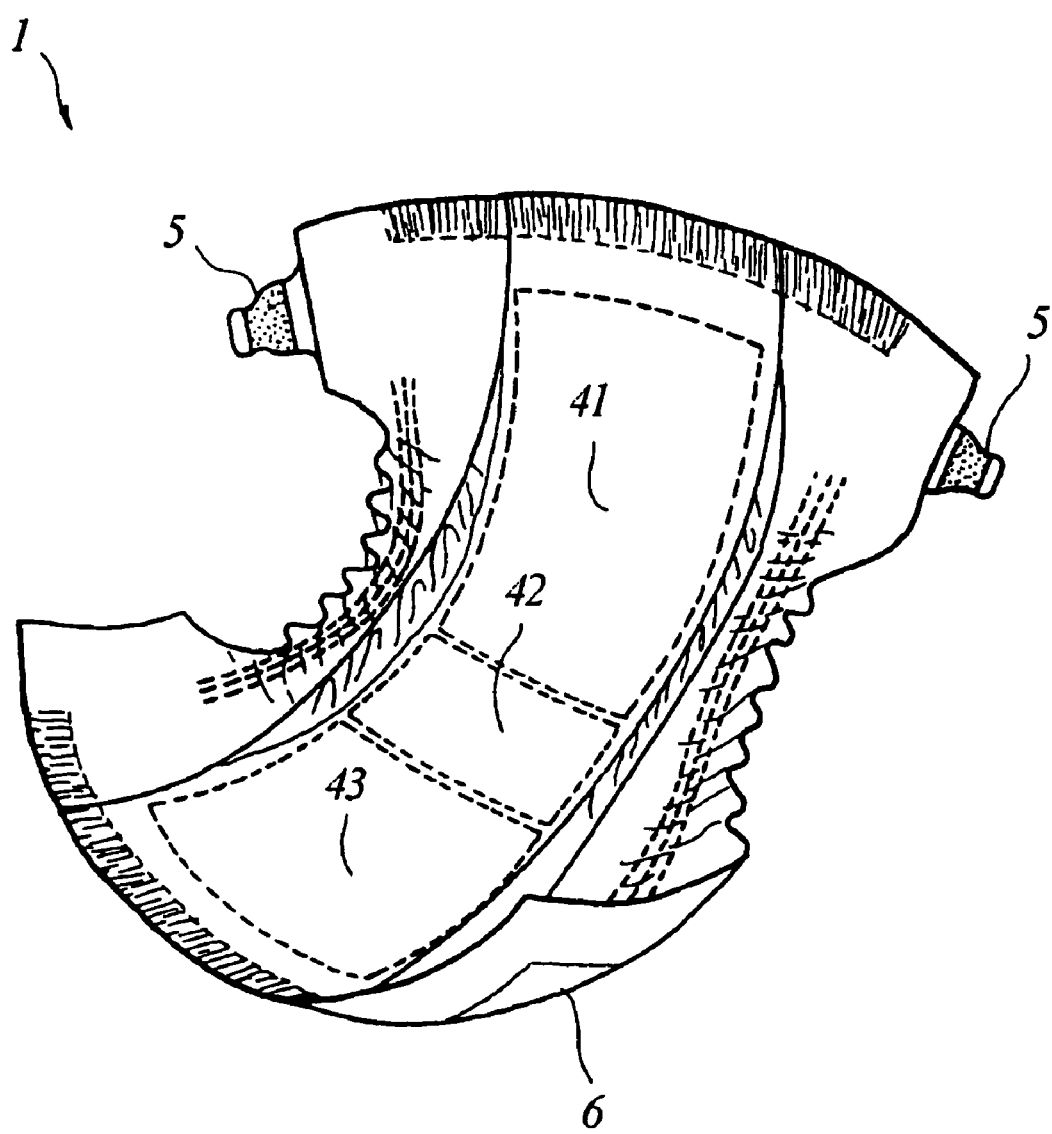
FIG. 1 is a schematic perspective view of a disposable diaper according to an embodiment of the present invention.
Figure 5A:
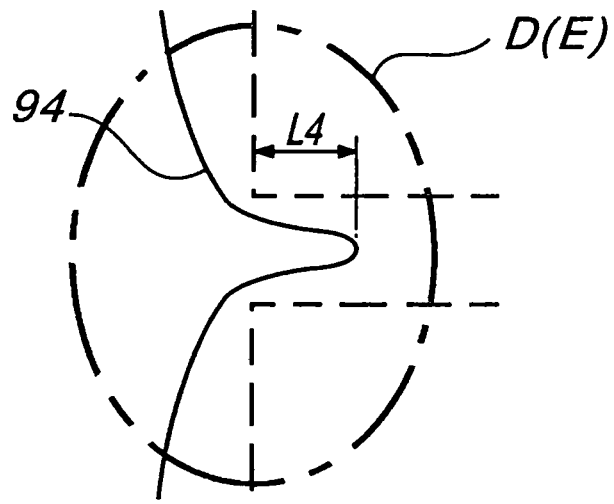
Figure 5B:
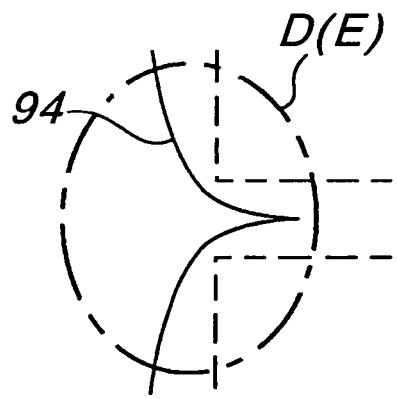
Figure 5C:
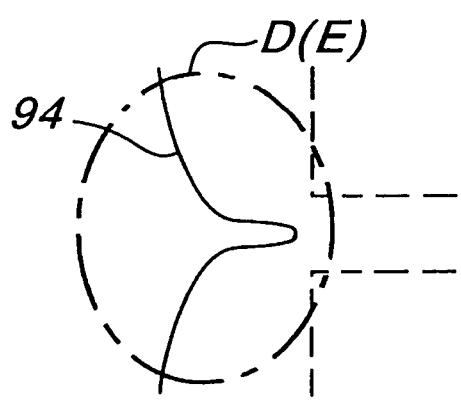

FIG. 5(a), FIG. 5(b), and FIG. 5(c) each show the form of the fixed end of standing gathers in the vicinity of the facing corners of adjacent absorbent members; in which FIG. 5(a) shows that of the disposable diaper of FIG. 1, and FIG. 5(b) and FIG. 5(c) give other examples.

BEST MODE FOR CARRYING OUT THE INVENTION

The present invention will be described in detail with reference to its preferred embodiment.

Figure 2:
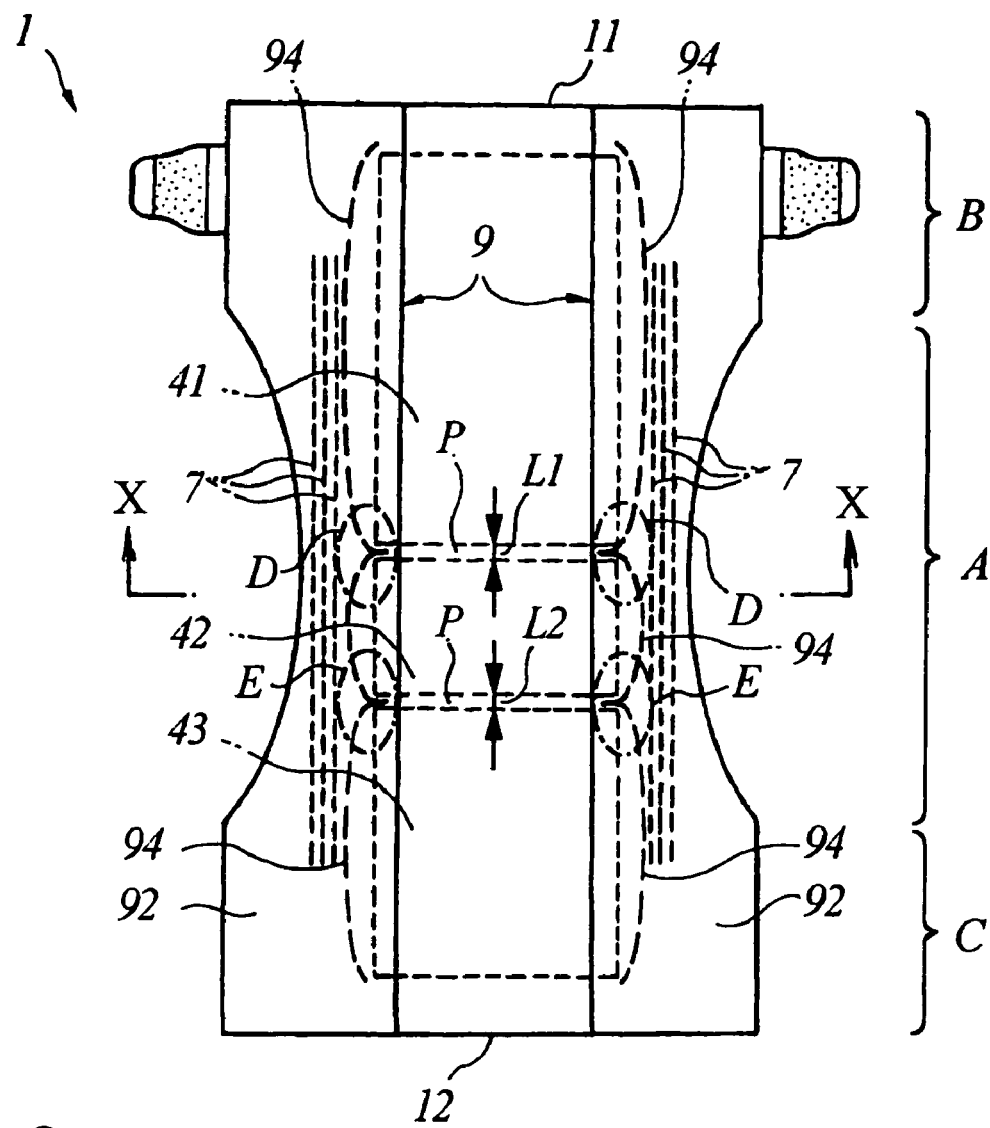
FIG. 2 is a plan view of the disposable diaper of FIG. 1 in its stretched flat state.
Figure 3:
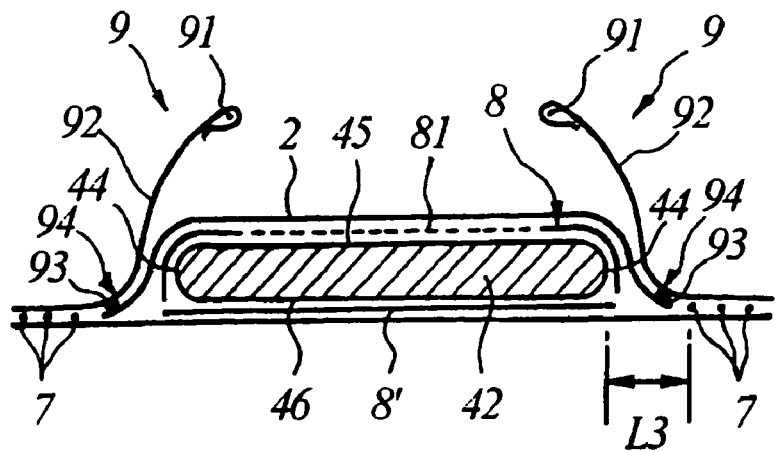
FIG. 3 is a schematic cross-sectional view taken along line X-X in FIG. 2.
Figure 4:
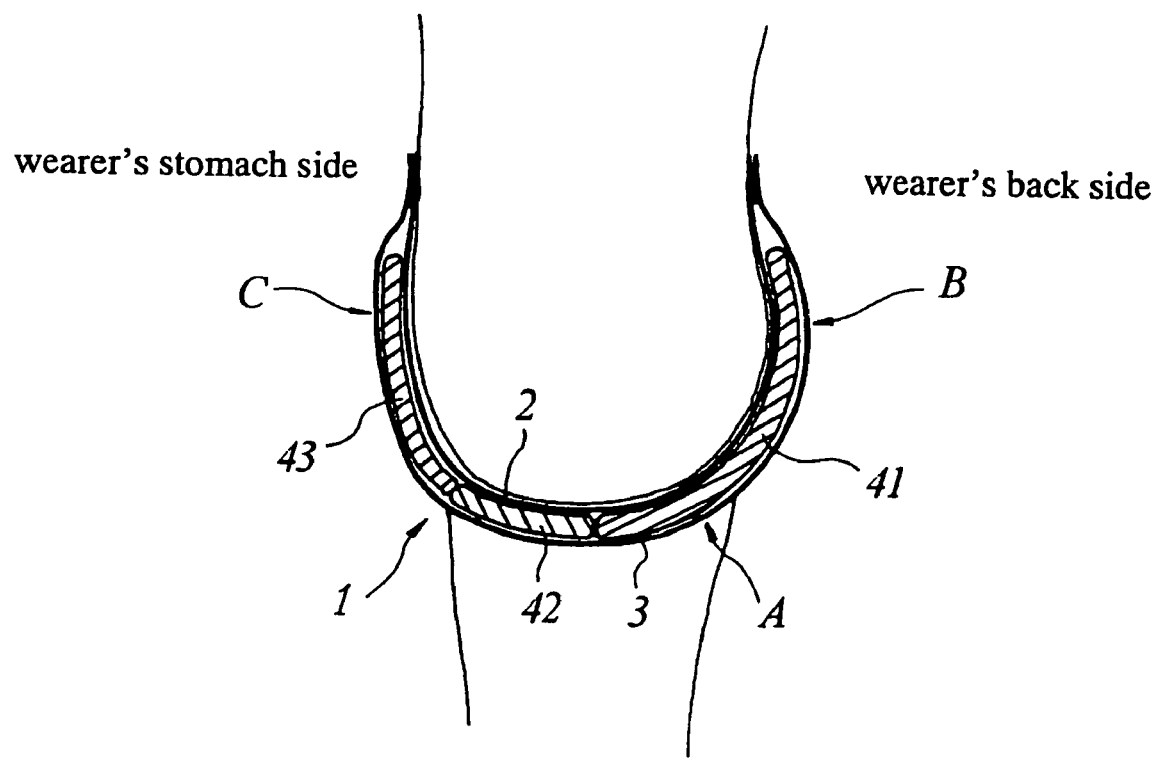
FIG. 4 is a schematic cross-sectional view of the disposable diaper of FIG. 2 in its worn state.

As shown in FIGS. 1 to 3, a disposable diaper 1 according to the embodiment contains a liquid permeable topsheet 2, a liquid impermeable backsheet 3, and a liquid retentive absorbent members 41 to 43 that are disposed between the two sheets. The disposable diaper 1 has a crotch portion A, which is positioned in the lengthwise middle of the diaper and adapted to be applied to the crotch of a wearer, and a rear portion B and a front portion C which are in the rear and the front of the crotch portion A, respectively.

The diaper 1 is a so-called fitted (tape type) diaper having a fastening tape 5 on both sides of the rear portion B and a landing zone 6 for receiving the fastening tapes 5 on the outer side of the front portion C.

The diaper 1 has arc-shaped sides in its crotch portion A to make the shape of a sandglass (with the lengthwise middle narrowed) as a whole. The backsheet 3 has the same sandglass-shaped contour as the diaper. The topsheet 2 is superposed on the widthwise middle region of the backsheet 3 with the absorbent members 41 to 43 sandwiched therebetween. The backsheet 3 extends outward from both longer side edges of the topsheet 2. A sheet 92 for forming standing gathers (described infra) is joined on each side extension of the backsheet 3.

The diaper 1 has three absorbent members 41, 42, and 43. As depicted in FIG. 2, the absorbent members 41 to 43 are arranged in series in the direction of from the rear portion B, through the crotch portion A, to the front portion C. The direction of "from the rear portion B, through the crotch portion A, to the front portion C" is the same as the direction of "from the front portion C through the crotch portion A, to the rear portion B". In the case of a fitted diaper of tape type that is almost a rectangle longer than wide like the diaper 1, that direction is defined to be a diaper length direction.

As shown in FIG. 2, the three absorbent members 41 to 43 are rectangles in their plan views and substantially equal in dimensions in the thickness and diaper width directions. The dimension of the absorbent members in the diaper length direction descends in the order of 41, 43, and 42. The boundary between the absorbent members 41 and 42 is positioned at almost the middle of the crotch portion A (i.e., almost the middle of the diaper length), and that between the absorbent members 42 and 43 is slightly apart from that middle position toward the front portion C.

An elastic member 7 is arranged in its stretched state on both sides of the series of the absorbent members 41 to 43, i.e., in the diaper length direction. There are a plurality of the elastic members 7 on each side of the diaper along the diaper length direction. The elastic members 7 are arranged along both sides of the absorbent members 41 to 43 in the areas slightly outside both the side edges of each absorbent member and fixed with an adhesive between the backsheet 3 and the respective sheets 92.

The elastic members 7 are disposed over a length between the absorbent member 41 that is the nearest to the waist edge 11 of the rear portion B and the absorbent member 43 that is the nearest to the waist edge 12 of the front portion C. In the present embodiment, the elastic members 7 also serve as elastic members for leg gather formation. That is, the elastic members 7 are disposed on the leg portions around wearer's legs to form leg gathers in the leg portions.

The absorbent members 41 to 43 are disposed such that a gap is produced between any two of them when the diaper is stretched flat and that any two of them come into close contact with each other while the diaper is worn.

Specifically, there is a gap P between the absorbent members 41 and 42 and between the absorbent members 42 and 43 when the diaper 1 is stretched flat as depicted in FIG. 2. While the diaper 1 is worn, on the other hand, the absorbent members 41 and 42 are brought into close contact, and the absorbent members 42 and 43 are brought into close contact, both by the contracting force of the elastic members 7.

That the adjacent absorbent members come into close contact while the diaper is worn does not mean that they should be always in close contact with each other while the diaper is worn. Where the absorbent members are each made of a fiber aggregate and/or a superabsorbent polymer, they may come into direct contact with each other or indirect contact via a nonwoven fabric 8, tissue paper or any other sheeting.

According to the present embodiment, the leg portions around wearer's legs contract by the elastic members 7 to provide a snug fit to the legs. At the same time, the widthwise middle region of the diaper 1 where the absorbent members 41 to 43 are disposed also gives a good fit to the wearer's crotch without causing the absorbent members to bag out. Thus, such inconveniences as liquid's staying in the crotch portion, overhydration, and leakage can be prevented.

In addition, since the adjacent absorbent members are brought into intimate contact while the diaper is worn, a combination of the absorbent members is equal or superior to a one-piece absorbent member longer than wide in absorptivity and leakproofness.

In order to enjoy enhancement of the above-described effects, the distances L1 and L2 (see FIG. 2) between the adjacent absorbent members are preferably 3 to 20 mm, more preferably 5 to 10 mm, when the diaper is stretched flat. The facing edges of any adjacent two of the absorbent members are preferably parallel to each other. For the same purpose, the elastic members 7 are preferably disposed over at least a length from part of the absorbent member 41 to part of the absorbent member 43, either with an overlap with the absorbent members 41 to 43 or in the area very near to the absorbent members 41 to 43. Where the elastic members 7 are disposed near the absorbent members, the smallest distance L3 (see FIG. 3) between the side edge of every absorbent member and the elastic members 7 is preferably 50 mm or shorter, more preferably 30 mm or shorter.

The absorbent members 41 to 43 of the diaper 1 according to the present embodiment are each made of a fiber aggregate and/or a superabsorbent polymer. As shown in FIG. 3, opposite side faces 44 extending in the diaper length direction and the skin-facing surface 45 (the surface on the side that is applied to the wearer's body) of every absorbent member are covered with a sheet of nonwoven fabric 8 that overlies to bridge the plurality of the absorbent members. The nonwoven fabric 8 is water-hydrophilic in a part 81 of the area covering the skin-facing surface 45 of each absorbent member, i.e., the diaper width middle area indicated by the dotted line. The nonwoven fabric 8 is water-repellent in the other area, i.e., the area covering the opposite side faces 44 and the skin-facing surface 45 except the part 81, of every absorbent member.

In the diaper 1 of the present embodiment, the gaps between the adjacent absorbent members contract following the contraction of the elastic members. Therefore, the material bridging the gaps and covering the absorbent members is required to be strong and flexible. Such requirements are sufficiently satisfied by using nonwoven fabric instead of tissue paper as a material covering the absorbent members made of a fiber aggregate and/or a superabsorbent polymer.

With the opposite side areas of the skin-facing surface and the opposite side faces of every absorbent member being covered with the water repellent part of the nonwoven fabric as in the diaper 1 of the present embodiment, there is obtained an advantage that once absorbed liquid hardly flows back. For application to elder infants who pass their urine at high flow rates, the rate of absorption may be too slow to keep up with the flow rate of urination. Therefore, the diaper according to this embodiment is suited for application to young infants.

The above-described nonwoven fabric 8 may be replaced with a nonwoven fabric that is water-hydrophilic in the area covering the entire skin-facing surface 45 of every absorbent member and water-repellent in the area covering the opposite side faces 44 of every absorbent member. In this case, the water-repellent area covers only the side faces of the absorbent members so that the absorbent members exhibit water wettability over a wider area. Accordingly, the diaper of this type is fit for elder infants or adults who pass a relatively large amount of urine. In the diaper 1, the non-skin-facing surface 46 of every absorbent member is covered with a second nonwoven fabric 8' bridging all the absorbent members.

The nonwoven fabric having a water-hydrophilic area and a water repellent area can be obtained by, for example, rendering a part of nonwoven fabric made of hydrophobic fiber water-hydrophilic by any known processing or making a part of nonwoven fabric made of hydrophilic fiber water-repellent by any known processing. Any nonwoven fabric produced by various processes can be used as a covering material. To satisfy both requirements for strength and flexibility, and the like, it is advisable to use SMS nonwoven (three-layered laminate having a spunbond/meltblown/spunbond structure), spun-bonded nonwoven, or heat-rolled nonwoven.

The diaper 1 of the present embodiment has standing gathers 9, 9 on both side portions thereof extending in the direction of from the rear portion B, through the crotch portion A, to the front portion C, i.e., in the diaper length direction. In more detail, the opposing standing gathers 9 are formed by fixing the respective standing gather-forming sheets 92 having the respective elastic members 91. Each sheet 92 is fixed along a longer side of the diaper such that it may cover an area of the topsheet 2 inward and outward about a longer side edge of the topsheet 2. Each sheet 92 is fixed to the topsheet 2 at a predetermined position in the diaper width direction by a joint 93. The joint 93 is made by known means, such as heat seal or an adhesive. The part fixed by the joint 93 is the fixed end 94 of the standing gathers. The area of each sheet 92 outside the fixed end 94 is fixed onto the topsheet 2 or the backsheet 3. The area of each sheet 92 inside the fixed end 94 and near each of the opposite lengthwise ends of the diaper are fixed onto the topsheet 2.

In the diaper 1 of the present embodiment, the fixed end 94 of the standing gathers 9 on each side is not linear but wavy along the diaper length direction as shown in FIG. 2. As shown in FIG. 5(*a*), a part of the fixed end 94 depicts a projection sticking toward the widthwise middle of the diaper in each of regions D and E that are in the vicinity of the facing corners of the adjacent absorbent members. More specifically, the fixed end 94 of the standing gathers 9 extends substantially in the diaper length direction but, in the region D near the facing corners of the absorbent members 41 and 42 and the region E near the facing corners of the absorbent members 42 and 43, the position of the fixed end 94 is shifted toward the widthwise middle of the diaper. As a result, when the diaper is stretched flat and seen from the side of its topsheet 2 the fixed end 94 is curved inward to the diaper widthwise middle to depict a projection. What is meant by the term "wavy" as used in the present invention is not limited to "having a strictly sinusoidal waveform" but includes "having a substantially sinusoidal waveform, such as the form shown in FIG. 5(*b*)".

In a diaper having a plurality of absorbent members arranged in series, diffusion of liquid in the diaper width direction is accelerated so that the demand for leakproofness of the standing gathers is stricter. Furthermore, liquid is apt to run in the diaper length direction between the side edges of the absorbent members and the standing gathers. Hence, by the standing gathers of which the fixed end is arranged in a wavy form with inward projections in parts as described above, the liquid flowing outward in the diaper width direction is returned inward in the diaper width direction, and the liquid running in the diaper length direction is once blocked and helped to be absorbed in the vicinity of the urination point of a wearer. Leakage in both the diaper width and length directions can be thus prevented effectively.

In the diaper 1 according to the present embodiment, the fixed ends 94 of the opposing standing gathers 9 intrude between the adjacent absorbent members, i.e., between the absorbent members 41 and 42 and between the absorbent members 42 and 43, as shown in FIG. 5(*a*). Therefore, the liquid running in the diaper length direction within the width of each absorbent member is effectively blocked by the standing gathers intruding from both sides. As a result, the standing gathers provide enhanced prevention against leakage particularly leakage in the diaper length direction. The intrusion length L4 (see FIG. 5(*a*)) of the fixed end 94 between the adjacent absorbent members is preferably such that the total intrusion length on both sides (e.g., L4×2) is more than 0% and not more than 10% of the width of the absorbent members (the dimension in the diaper width direction).

Materials making up the diaper 1 of the present invention will now be described. The topsheet 2, the backsheet 3, the standing gather-forming elastic members 91, and the standing gather-forming sheets 92 can be of any material chosen from among various kinds heretofore employed in absorbent articles including disposable diapers and sanitary napkins.

The fiber aggregate making part of, or the whole of, the absorbent members 41 to 43 may be either a nonwoven fabric or a fiber web. Constituent fibers include pulp fiber, cellulosic fibers such as rayon and cotton, polyolefin fibers such as polyethylene and polypropylene, polycondensation fibers such as polyester (e.g., polyethylene terephthalate) and polyamide, and vinyl polymers such as polyvinyl chloride and polyvinyl acetate. The fibers may be single-component fiber or conjugate fiber of side-by-side configuration, sheath-core configuration, etc.

Any known superabsorbent polymer can be used to make part of, or the whole of, each of the absorbent members 41 to 43. Examples of useful superabsorbent polymers are sodium polyacrylate, an acrylic acid-vinyl alcohol copolymer, crosslinked sodium polyacrylate, a starch-acrylic acid graft copolymer, an isobutylene-maleic anhydride copolymer or a saponification product thereof, and polyaspartic acid.

Each of the absorbent members used in the present invention may be made solely of a fiber aggregate or a superabsorbent polymer but is preferably made of a combination of a fiber aggregate and a superabsorbent polymer. The superabsorbent polymer can be present as dispersed in the fiber interstices of a fiber aggregate or sandwiched in between nonwoven fabrics or fiber webs made of a fiber material.

Materials of the elastic members 7 include synthetic rubber, natural rubber, and Spandex and the like. The form of the elastic members 7 includes not only yarn but tape and film and the like.

The present invention is not construed as being limited to the above-mentioned embodiment, and various changes and modifications can be made therein without departing from the spirit and scope thereof.

For example, while the above-described diaper 1 has three absorbent members laid out in series, the diaper can have two or more than three absorbent members arranged in series. All the absorbent members used in one diaper may be equal in dimension in the diaper length direction, or at least one of them may be different in dimension in the diaper length direction. The same applies to the thickness and the dimension in the diaper width direction.

The part of the standing gathers' fixed end located in the vicinities of the facing corners of adjacent absorbent members can have the form shown in FIG. 5(*b*) or FIG. 5(*c*) instead of the form shown in FIG. 5(*a*).

In order to bring the adjacent absorbent members into close contact more surely, a second elastic member may be disposed in its stretched state in the diaper widthwise middle to extend in the diaper length direction, in addition to the elastic members 7 provided on both longer sides of the diaper. The number of the elastic member 7 arranged on the both sides in the diaper length direction may be one on each side.

The disposable diaper according to the present invention may be of pull-on type.

INDUSTRIAL APPLICABILITY

The disposable diaper of the present invention provides a snug fit with little bagging of its absorbent member while worn.

The invention claimed is:

1. A disposable diaper comprising a liquid permeable topsheet, a liquid impermeable backsheet and three liquid retentive absorbent members interposed between the topsheet and the backsheet, said three absorbent members being disposed in series in the direction of from the rear portion, through the crotch portion, to the front portion of the diaper, and wherein the length of the three absorbent members descends in the order of the rear portion absorbent member, the front portion absorbent member and the crotch portion absorbent member, elastic members being disposed in a stretched state on both sides of said series of said three absorbent members, such that when said diaper is worn, the elastic members are disposed on the leg portions around the wearer's legs, and wherein the elastic members are disposed longitudinally on both lateral sides of the disposable diaper from the rear portion absorbent member to the front portion absorbent member, said absorbent members being arranged such that a gap, wherein said gap extends in a width direction of said diaper, is produced between any adjacent two of said three absorbent members when the diaper is stretched flat and that any adjacent two of said three absorbent members come into close contact with each other when the diaper is worn; and wherein a boundary between the absorbent members in the rear and crotch portions is positioned at about the middle of the diaper length, and a boundary between the absorbent members in the crotch portion and front portion is slightly before the middle of the diaper length and toward the front of the diaper.

2. The disposable diaper according to claim 1, wherein each of said absorbent members comprises a fiber aggregate and/or a superabsorbent polymer, the opposite side faces of each of said absorbent members which extend in the diaper length direction and the skin-facing surface of each of said absorbent members are covered with a sheet of nonwoven fabric which bridges said absorbent members, and said nonwoven fabric is water-hydrophilic in a part or the whole of the area covering said skin-facing surface of each of said absorbent members and is water-repellent in the area covering said opposite side faces of each of said absorbent members.

3. The disposable diaper according to claim 1, wherein standing gathers are provided on both sides of the diaper along the direction of from the rear portion, through the crotch portion, to the front portion of the diaper, said standing gathers on each side being formed by fixing a standing gather-forming sheet having an elastic member along each of the longer sides of the diaper such that said sheet covers an area of the topsheet inward and outward about each of the longer side edges of the topsheet.

4. The disposable diaper according to claim 1, wherein standing gathers are provided on each side of the diaper along the direction of from the rear portion, through the crotch portion, to the front portion, the fixed end of said standing gathers on each side depicting a wavy line, and part of said fixed end depicting a projection toward the widthwise middle of the diaper in the vicinity of the facing corners of any adjacent two of said absorbent members.

5. The disposable diaper according to claim 4, wherein said part of said fixed end intrudes between said any adjacent two of said absorbent members.

* * * * *